United States Patent [19]

Haytko et al.

[11] Patent Number: 5,202,029
[45] Date of Patent: Apr. 13, 1993

[54] PROCESS FOR PURIFICATION OF HMG-COA REDUCTASE INHIBITORS

[75] Inventors: Peter N. Haytko, Rahway; Arthur S. Wildman, Jr., Martinsville, both of N.J.

[73] Assignee: Caron Kabushiki Kaisha, Tokyo, Japan

[21] Appl. No.: 668,831

[22] Filed: Mar. 13, 1991

[51] Int. Cl.$^5$ .............................................. B01D 15/08
[52] U.S. Cl. .................... 210/656; 210/198.2; 422/70; 435/125; 436/161; 514/460; 514/824; 549/292
[58] Field of Search ............ 210/656, 635, 198.2, 210/770; 436/161; 435/125; 549/292; 422/70; 514/460, 824

[56] References Cited

U.S. PATENT DOCUMENTS

| | | |
|---|---|---|
| 4,231,938 | 11/1980 | Monaghan et al. .............. 435/125 |
| 4,533,494 | 8/1985 | Urchiyama et al. ............. 530/309 |
| 4,719,229 | 1/1988 | Reamer et al. ................. 549/292 |
| 4,778,600 | 10/1988 | Williams ...................... 210/198.2 |
| 4,833,258 | 5/1989 | Smith et al. ................... 549/292 |
| 4,965,200 | 10/1990 | Chen et al. .................... 435/125 |
| 4,997,755 | 3/1991 | Williamson et al. ............ 435/125 |
| 4,997,849 | 3/1991 | Petuch et al. .................. 549/292 |

OTHER PUBLICATIONS

R. H. Perry and C. H. Chilton, "Chemical Engineering Handbook", McGraw-Hill, 1973, New York (pp. 17-8~17-13).
Bird, Br. Med. Journal, 299; 783-787 (1989).

Primary Examiner—Robert A. Dawson
Assistant Examiner—Sun Uk Kim

[57] ABSTRACT

A process for the purification of an HMG-CoA reductase inhibitor employing preparative high performance liquid chromatography is described.

10 Claims, No Drawings

PROCESS FOR PURIFICATION OF HMG-COA REDUCTASE INHIBITORS

BACKGROUND OF THE INVENTION

High product purity is an important criterion for the manufacture of a safe and effective pharmaceutical. HMG-CoA reductase inhibitors, such as lovastatin, simvastatin and pravastatin, are a recently introduced new class of cholesterol-lowering agents that effectively lower plasma cholesterol but must be taken on a long term basis. Thus it is particularly critical that HMG-CoA reductase inhibitors be administered in the highest possible purity.

The present purification procedure for HMG-CoA reductase inhibitors involves a solid absorption operation and at least two recrystallizations. This procedure yields a product purity of ~99.0%. It would be highly desirable to employ a purification process that would yield a product purity greater than 99.5% and use no more than one recrystallization with a recyclable solvent and be adaptable to a high production volume.

High performance liquid chromatography (HPLC) is commonly used for the analytical determinations of compound purity. HPLC for large scale industrial solution preparations (preparative HPLC) has been employed in the separation and and purification of proteins but it is believed not to have been employed in the large scale purification of relatively small molecules such as HMG-CoA reductase inhibitors.

DETAILED DESCRIPTION OF THE INVENTION

This invention relates to a process for the purification of HMG-CoA reductase inhibitors by high performance liquid chromatography to yield a product of purity greater than 99.5%. The HMG-CoA reductase inhibitors within this invention include, but are not limited to, lovastatin, simvastatin, pravastatin, fluvastatin and mevastatin. Surprisingly, the product purity obtained through HPLC is higher than that achieved by conventional crystallization processes even after repeated crystallizations. Furthermore, the HPLC procedure offers a significant advantage in that only one crystallization procedure is required and the process may be carried out with only one organic solvent minimizing the need for recycling in an industrial process.

The procedure employed herein may either be normal phase HPLC wherein the packing silica may be uncoated or reverse phase HPLC wherein the packing material is silica coated with a hydrophobic binding group or a porous graphitic carbon. For HMG-CoA reductase inhibitors exhibiting a tetrahydropyranone ring, such as lovastatin and simvastatin, the reverse phase procedure is preferred. It should be understood that coating here includes both a physical and a chemical bonding of the binding group.

The crude HMG-CoA reductase inhibitor is dissolved in an organic solvent or a solution of an organic solvent and water. The mixture may be buffered to a pH between 2 and 9 with an organic or inorganic salt. Buffers may include but are not limited to Tris-acetate, or acetic acid/ammonia. The resulting solution is placed on an HPLC column packed with silica or a porous graphitic carbon. Depending on whether the chromatography is normal or reverse phase, the packing silica may be uncoated (normal phase) or it may be coated (reverse phase) with a hydrophobic coating material such as an organosilyl or cyano-organosilyl stationary phase or a polystyrene-divinylbenzene copolymer coated with an organosilyl stationary phase.

The column diameter may vary from 5 cm to 80 cm. In general the column is packed with the coated or uncoated silica in the following manner: Approximately 758 grams of packing material is slurried in ethanol to a total slurry volume of 2.8 liters. The slurry is then transferred into the column and compressed at 55 bar using Dynamic Axial Compression (D.A.C. ®), a procedure described in U.S. Pat. No. 3,996,609 and Fr 73.07278. The bed produced is 8.0 cm by 25.0 cm. The ethanol is removed by employing a duplex diaphragm pump with a capacity of 900 ml/min to pump eluant through the column. The eluant is an organic solvent or a solution of an organic solvent and water which may also include a buffer of pH 2 to pH 9. The eluant is generally the same solvent solvent mixture as the dissolving solvent but, if desired, the eluant may have a different composition. Preferably the eluant has as the same organic solvent/water composition as the dissolving solvent. If desired, a gradient elution of the mobile phase may be employed to more rapidly elute the HMG-CoA reductase inhibitor through the column. The chromatography may be carried out at any operating temperature appropriate to the solvents employed, however a range of 15° to 60° C. is preferred. Detection of the HMG-CoA reductase inhibitor may be by spectroscopic means or by other physical means such as optical rotation or refractive index. The preferred means are by ultraviolet absorption or refractive index. After the HMG-CoA reductase inhibitor peak is collected, a portion of the solvent is removed and an aqueous medium added to crystallize the HMG-CoA reductase inhibitor. Generally, about one-third of the solvent mixture is removed and water is employed to crystallize out the HMG-CoA reductase inhibitor. Alternatively about two-thirds of the solvent mixture is removed to crystallize out the HMG-CoA reductase inhibitor. The crystallized inhibitor is then filtered and dried to yield a product of purity greater than 99.5% and with an overall yield of about 90%.

The crude HMG-CoA reductase inhibitor is prepared following any of the literature procedures well known to those skilled in this art. Packing materials of uncoated or coated silica are commercially available. Porous graphitic carbon as a packing material is also commercially available in pre-packed columns.

The organic solvent, employed as the dissolving solvent or the eluant, is selected from acetonitrile, methanol, ethanol, acetone, tetrahydrofuran, isopropanol, ethyl acetate, methylene chloride, chloroform or a mixture thereof. The percent of organic solvent in an organic solvent/water mixture may vary from 10% to 90% organic solvent, preferably 65% to 75% organic solvent.

EXAMPLE 1

4.6 g of crude lovastatin was dissolved in 200 ml of 70:30 acetonitrile/water which was injected onto a 5 cm diameter stainless steel column packed with 25 cm of C18 silica HPLC packing. The eluent was 70:30 acetonitrile/water and the flow rate was approximately 150 ml/min. The pure lovastatin fraction was collected in a volume of 260 ml using UV detection at 238 nm. The resulting solution was concentrated by removal of one-third of the solvent and the lovastatin crystallized by the addition of water to give an acetonitrile concentration of approximately 20–25%. The pure lovastatin product was recovered by filtration and drying. Lovastatin with a purity of 99.7% w/w was recovered in an overall yield of 90%.

EXAMPLE 2

Lovastatin at a concentration of 2.3 gm/100 ml was dissolved in a mixture of 70% acetonitrile/30% 0.02M Tris-acetate pH 7.4. The solution was injected onto a 5 cm stainless steel column packed with 25 cm of silica coated with an octadecyldimethylsilyl stationary phase. The eluent was 70% acetonitrile/30% water and the flow rate was approximately 150 ml/minute. Detection was by ultraviolet absorption at 238 nm. The lovastatin peak was collected and ½ the volume was removed by vacuum distillation at ≦40° C. Water is added to bring the acetonitrile concentration to 20–25%. The lovastatin is filtered and dried in vacuo at ≦40° C. Lovastatin with a purity of ≧99.7% was recovered in an overall yield of ≧90%.

EXAMPLE 3

4.6 g of crude lovastatin was dissolved in 200 ml of 70:30 acetonitrile/water buffered with 0.02M Tris-acetate (pH 7.5). The solution was injected onto a 5 cm diameter column packed with 25 cm of C18 silica HPLC packing. The eluent was 70:30 acetonitrile/water and the flow rate was approximately 150 ml/min. The pure lovastatin fraction was collected in a volume of 265 ml using UV detection at 238 nm. The resulting solution was concentrated by removal of one-third of the solvent and the lovastatin crystallized by the addition of water to give an acetonitrile concentration of approximately 20–25%. The pure lovastatin product was recovered by filtration and drying. Lovastatin with a purity of 99.7% w/w was recovered in an overall yield of 91%.

EXAMPLE 4

4.6 g of crude lovastatin was dissolved in 200 ml of 70:30 acetonitrile/water buffered with 0.02M Tris-acetate (pH 7.5). The solution was injected onto a 5 cm diameter column packed with 25 cm of C18 silica HPLC packing. The eluent was 70:30 acetonitrile/water and the flow rate was approximately 150 ml/min. The pure lovastatin fraction was collected in a volume of 265 ml using UV detection at 238 nm. The resulting solution was concentrated by removal of two-thirds of the solvent resulting in the crystallization of the lovastatin. The pure lovastatin product was recovered by filtration and drying. Lovastatin with a purity of 99.7% w/w was recovered in an overall yield of 91%.

EXAMPLE 5

Lovastatin at a concentration of 4.5 gm/100 ml was dissolved in a mixture of 70% acetonitrile/30% 0.02M Tris-acetate pH 7.2. The 40° C. solution was injected onto a 5 cm stainless steel column packed with 25 cm of C18 silica HPLC packing. The eluent was 70:30 acetonitrile/water at 40° C. and the flow rate was approximately 150 ml/min. The pure lovastatin fraction was collected in a volume of 500 ml using UV detection at 238 nm. The resulting solution was concentrated by removal of one-third of the solvent and the lovastatin crystallized by the addition of water to give an acetonitrile concentration of approximately 20–25%. The pure lovastatin production was recovered by filtration and drying. Lovastatin with a purity 99.8% w/w was recovered in an overall yield of 90%.

What is claimed is:

1. A process for purifying a crude HMG-CoA reductase inhibitor which comprises:
   (1) placing a solution of the crude HMG-CoA reductase inhibitor on a high performance liquid chromatography column wherein the column is packed with silica optionally coated with a stationary phase selected from the group consisting of a triorganosilyl, a cyanoorganosilyl and a polystyrene-divinylbenzene copolymer with an organosilyl, or the column is packed with a porous graphitic carbon;
   (2) eluting the crude HMG-CoA reductase inhibitor with a solvent mixture comprising:
      (a) an organic solvent selected from the group consisting of acetonitrile, methanol, ethanol, acetone, tetrahydrofuran, isopropanol, ethyl acetate, methylene chloride and chloroform, or a mixture thereof and optionally
      (b) water or an aqueous solution selected from the group consisting of phosphoric acid and acetic acid;
   (3) removing a portion of the solvent mixture from the eluted HMG-CoA reductase inhibitor; and
   (4) treating the eluted HMG-CoA reductase inhibitor with water to crystallize a purified HMG-CoA reductase inhibitor of purity ≧99.5%.

2. The process of claim 1 wherein the HMG-CoA reductase inhibitor is selected from the group consisting of lovastatin, simvastatin, pravastatin, fluvastatin and mevastatin.

3. The process of claim 2 wherein the HMG-CoA reductase inhibitor is selected from the group consisting of lovastatin and simvastatin.

4. The process of claim 3 wherein the column is packed with silica coated with an octadecyldimethylsilyl stationary phase.

5. The process of claim 4 wherein the solvent mixture is acetonitrile and water.

6. The process of claim 5 wherein the solvent mixture is 70% acetonitrile and 30% water.

7. The process of claim 6 wherein the column and the solvent mixture are maintained between 15° and 60° C.

8. The process of claim 1 further comprising filtering and drying of the purified HMG-CoA reductase inhibitor to yield a product of purity ≧99.5%.

9. A process of claim 1 wherein step(3) 30 to 35 percent of the solvent mixture is removed.

10. A process for purifying a crude HMG-CoA reductase inhibitor which comprises:
   (1) placing a solution of the crude HMG-CoA reductase inhibitor on a high performance liquid chromatography column wherein the column is packed with silica optionally coated with a stationary phase selected from the group consisting of triorganosilyl, a cyanoorganosilyl and a polystyrene-divinylbenzene copolymer with an organosilyl, or the column is packed with a porous graphitic carbon;
   (2) eluting with a solvent mixture comprising:
      (a) an organic solvent selected from the group consisting of acetonitrile, methanol, ethanol, acetone, tetrahydrofuran, isopropanol, ethyl acetate, methylene chloride and chloroform, or a mixture thereof and optionally,
      (b) water or an aqueous solution selected from the group consisting of phosphoric acid and acetic acid; and
   (3) removing about 60 to 65% of the solvent mixture to crystallize a purified HMG-CoA reductase inhibitor of purity ≧99.5%.

UNITED STATES PATENT AND TRADEMARK OFFICE
CERTIFICATE OF CORRECTION

PATENT NO. : 5,202,029
DATED : April 13, 1993
INVENTOR(S) : P. N. Haytko et al.

It is certified that error appears in the above-identified patent and that said Letters Patent is hereby corrected as shown below:

On title page, Item [73], delete "Caron Kabushiki Kaisha, Tokyo, Japan" and in its place insert --Merck & Co., Inc., Rahway, New Jersey.--.

Signed and Sealed this

Twelfth Day of April, 1994

Attest:

BRUCE LEHMAN

*Attesting Officer*      Commissioner of Patents and Trademarks